United States Patent
Jirka et al.

(10) Patent No.: US 10,532,146 B2
(45) Date of Patent: Jan. 14, 2020

(54) APPARATUS FOR EXTRA-CORPOREAL BLOOD TREATMENT AND METHOD OF PRESETTING AN INITIAL MODE OF TREATMENT FOR AN EXTRA-CORPOREAL BLOOD TREATMENT APPARATUS

(71) Applicants: Fresenius Medical Care Deutschland GmbH, Bad Homburg v.d.H. (DE); Fresenius Medical Care - DS, s.r.o, Prague (CZ)

(72) Inventors: Tomas Jirka, Vojkovice (CZ); Joerg Jonas, Bogota (CO); Volker Nier, Reichelsheim (DE); Wolfgang Wehmeyer, Tuebingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 420 days.

(21) Appl. No.: 13/911,379

(22) Filed: Jun. 6, 2013

(65) Prior Publication Data
US 2013/0327713 A1    Dec. 12, 2013

Related U.S. Application Data

(60) Provisional application No. 61/656,058, filed on Jun. 6, 2012.

(30) Foreign Application Priority Data

Jun. 6, 2012 (DE) .................. 10 2012 011 196

(51) Int. Cl.
*A61M 1/36* (2006.01)
(52) U.S. Cl.
CPC ................. *A61M 1/3663* (2013.01)

(58) Field of Classification Search
CPC ...... A61M 1/16; A61M 1/1635; A61M 1/165; A61M 1/1694; A61M 1/3413;
(Continued)

(56) References Cited

U.S. PATENT DOCUMENTS

| 4,234,428 A | 11/1980 | Schnell |
| 4,469,593 A * | 9/1984 | Ishihara ............... A61M 1/16 |
| | | 210/104 |

(Continued)

FOREIGN PATENT DOCUMENTS

| DE | 32 23 051 A1 | 12/1983 |
| DE | 3223051 | 12/1983 |

(Continued)

OTHER PUBLICATIONS

Hoerl, W.H. und Wanner, C. (Hrsg.) Dialyseverfahren in Klinik und Praxis, 6. Aufl., S. 180, 181, 368 und 369, Georg Thieme Verlag 2003.

(Continued)

*Primary Examiner* — Krishnan S Menon
*Assistant Examiner* — Brad Gordon
(74) *Attorney, Agent, or Firm* — Kilyk & Bowersox, P.L.L.C.

(57) ABSTRACT

An apparatus for extra-corporeal blood treatment and a method of presetting an initial mode of treatment in the opening phase of an extra-corporeal blood treatment are controlled based on the opening phase of a haemodiafiltration, in which particularly fast removal of electrolytes such as potassium or of urea occurs. The apparatus has a control and computing unit for presetting an initial mode of treatment, in which over a preset interval of time, substituate is fed to the extra-corporeal blood circuit, dialysis fluid is not fed through the dialyser and instead only ultrafiltrate is withdrawn from the dialyser and, on expiry of the preset (Continued)

interval of time, dialysis fluid is fed through the dialyser. Alternatively, dialysis fluid is provided during the preset interval of time through the dialyser at a dialysis fluid flow rate that is smaller than the dialysis fluid flow rate after the preset interval of time has elapsed.

27 Claims, 2 Drawing Sheets

(58) Field of Classification Search
CPC .. A61M 1/342; A61M 1/3431; A61M 1/3437; A61M 1/3441; A61M 1/3624; A61M 1/3663; A61M 2205/3334; A61M 1/1609; A61M 1/1607; A61M 1/1639; A61M 1/361; A61M 1/3612; A61M 1/1656; A61M 1/1696; A61M 1/28; A61M 1/3465; A61M 1/3639
USPC .......................... 137/115.01, 2; 210/138, 646
See application file for complete search history.

(56) References Cited

U.S. PATENT DOCUMENTS

| | | | |
|---|---|---|---|
| 4,508,622 A | | 4/1985 | Polaschegg |
| 4,702,829 A | | 10/1987 | Polaschegg et al. |
| 4,711,715 A | * | 12/1987 | Polaschegg ............ A61M 1/16 210/103 |
| 5,366,630 A | * | 11/1994 | Chevallet ............ A61M 1/3441 210/138 |
| 6,083,187 A | * | 7/2000 | Nakayama .......... A61M 1/3441 604/6.01 |
| 6,187,207 B1 | | 2/2001 | Brauer |
| 6,284,141 B1 | | 9/2001 | Shaldon et al. |
| 6,821,421 B2 | | 11/2004 | Murakami |
| 2004/0011722 A1 | * | 1/2004 | Murakami .............. A61M 1/16 210/321.71 |
| 2006/0254982 A1 | * | 11/2006 | Kopperschmidt .... A61M 1/342 210/646 |
| 2010/0264086 A1 | * | 10/2010 | Noack et al. ................. 210/647 |
| 2010/0274172 A1 | * | 10/2010 | Guenther ............. A61M 1/342 604/6.11 |

FOREIGN PATENT DOCUMENTS

| | | |
|---|---|---|
| EP | 0160272 | 11/1985 |
| EP | 0189561 A1 | 8/1986 |
| EP | 0974371 A2 | 1/2000 |
| EP | 1 595 560 A1 | 11/2005 |
| EP | 1595560 | 11/2005 |
| EP | 2238996 A1 | 10/2010 |
| EP | 2203198 B1 | 1/2017 |
| GB | 2246718 B | 2/1992 |
| JP | 2004-049493 A | 2/2004 |
| JP | 2004049493 A * | 2/2004 |
| JP | 2007-268257 A1 | 10/2007 |
| WO | 2009144522 A1 | 12/2009 |

OTHER PUBLICATIONS

International Preliminary Report on Patentability and Written Opinion dated Dec. 9, 2014 in PCT/EP2013/001608.
International Search Report in PCT/EP2013/001608 dated Aug. 30, 2013.
Schreiber, Christian et al., "69 Grundlagen der Nieren—und Leberdialyse," E Wintermantel, S.-W. Ha Medizintechnik—Life Science Engineering, Springer, (2009), pp. 1519-1584, English-language Abstract only.
B Braun "Dialysegerät Dialog," 16-8 GBA 38910273DE / Rev. 2.11.00 / Dec. 2011.
Hörl, W.H., et al. Dialyseverfahren in Klinik und Praxis, 6. Aufl., S. GeorgThieme Verlag (2003), pp. 180-183.
Meyer, Günther, Akute und chronische Hämodialyse, Pabst Science Publishers (1999), p. 5, 102-109.
"Description of "EC Motor Redesign" along to the applied CRS-Update," B. Braun Avitum, Version 1.0, 2 pages.

* cited by examiner

Appendix:

APPARATUS FOR EXTRA-CORPOREAL BLOOD TREATMENT AND METHOD OF PRESETTING AN INITIAL MODE OF TREATMENT FOR AN EXTRA-CORPOREAL BLOOD TREATMENT APPARATUS

CROSS REFERENCE TO RELATED APPLICATIONS

The present application claims priority to U.S. Provisional Patent Application Ser. No. 61/656,058, filed on Jun. 6, 2012, and claims priority to Application No. DE 10 2012 011 196.7, filed in the Federal Republic of Germany on Jun. 6, 2012, each of which is hereby expressly incorporated herein in its entirety thereto.

FIELD OF INVENTION

The present invention relates to an apparatus for extra-corporeal blood treatment having an extra-corporeal blood circuit which includes a first chamber of a dialyser or filter which is divided into the first and a second chamber by a semi-permeable membrane, and having a dialysis fluid system which includes the second chamber of the dialyser or filter. As well as this, the present invention also relates to a method of presetting an initial mode of treatment taking place in the opening phase of an extra-corporeal blood treatment performed by an extra-corporeal blood treatment apparatus.

BACKGROUND INFORMATION

In cases of chronic kidney failure, various methods of extra-corporeal blood treatment are used to remove substances needing to be excreted and to withdraw fluid. Whereas in haemodialysis (HD), the movement of substances of low molecular weight through the semi-permeable membrane (in the form of diffusion) is determined essentially by the differences in concentration between the dialysis fluid and the blood, in haemofiltration (HF), substances dissolved in the plasma of the blood, and particularly substances of higher molecular weight, are removed effectively by a high rate of fluid flow (convection) through the membrane of the dialyser. In haemofiltration, the dialyser acts as a filter. Haemodiafiltration (HDF) is a combination of these two methods.

In haemodiafiltration, some of the ultrafiltrate withdrawn through the membrane of the dialyser or filter is replaced by a sterile substitute fluid (a substitute) which is fed into the extra-corporeal blood circuit either upstream or downstream of the dialyser. The infeed of substitute upstream of the dialyser is referred to as pre-dilution, and the infeed downstream of the dialyser is referred to as post-dilution.

There are known pieces of apparatus for haemodiafiltration in which the dialysis fluid is produced on-line from fresh water and a concentrate and the substituate is obtained on-line from the dialysis fluid. In the known pieces of haemodiafiltration apparatus, the substituate in the extra-corporeal blood circuit is fed in from the dialysis fluid system of the apparatus via a substituate line. Pieces of haemodiafiltration apparatus are described, for example, in European Application Nos. EP 0 974 371 A3 and EP 1 595 560 A1.

In individual cases, complications may occur in dialysis due to shifts in the levels of electrolytes, leading to headaches or psychomotor disorders in patients. These complications are known as disequilibrium syndrome.

Disequilibrium syndrome is described in German Application No. DE 32 23 051 A1. German Application No. DE 32 23 051 A1 describes a dialysis apparatus in which the composition of the dialysis fluid is regulated during the dialysis treatment as a function of the electrolyte content of the dialysis fluid upstream and downstream of the dialyser. The electrolyte content of the dialysis fluid is measured by sensors arranged upstream and downstream of the dialyser.

SUMMARY

An object underlying the present invention is to provide an apparatus for extra-corporeal blood treatment which can be operated with a reduced risk to the patient of complications occurring. A further object of the present invention is to specify a method of presetting a mode of treatment in order to avoid complications during the extra-corporeal blood treatment.

It has been found that disequilibrium syndrome is attributable to shifts in the levels of electrolytes during the extra-corporeal blood treatment. Any excessive reduction of electrolytes, and in particular potassium, or the excessive reduction of urea, should therefore be avoided in the course of the extra-corporeal blood treatment.

The present invention is based on the finding that it is precisely during the first phase of a haemodiafiltration that particularly fast removal of electrolytes such as potassium or of urea occurs. The present invention is thus based on the principle of avoiding the excessive reduction of electrolytes in the opening phase of the extra-corporeal blood treatment.

To avoid an excessive reduction of electrolytes or an excessive reduction of urea, the present invention makes provision for an initial mode of treatment in which the extra-corporeal blood treatment apparatus is operated within a preset time interval only as a haemofiltration apparatus. During the haemofiltration, the rate of flow of the dialysis fluid is zero, only plasma being withdrawn via the membrane of the filter. The exchange rates of electrolytes such as potassium or of urea go down in the initial phase of the extra-corporeal blood treatment because the removal of electrolytes or urea takes place predominantly by diffusion and in haemofiltration, in contrast to haemodialysis, there is a convective metabolic exchange.

The quantity of fluid withdrawn from the patient in the opening phase of the blood treatment is fed back to the patient as substituate. The blood treatment using the parameters preset by the physician follows on from the opening phase of the blood treatment performed in the initial mode of treatment.

To avoid an excessive reduction of electrolytes or of urea in the initial treatment mode, an alternative embodiment makes provision for a delivery of dialysis fluid at a first dialysis fluid rate, which is smaller than the second dialysis fluid rate with which the dialysis fluid is delivered after the predetermined time interval has elapsed. In this connection, it should be understood that the first and second dialysis fluid rates are not necessarily constant. In this respect, an average fluid rate can also be understood. For the present invention, it is important that the dialysis fluid rates in the initial treatment mode are smaller than in a treatment mode following the initial treatment mode. Preferably, the first dialysis fluid rate should be very much smaller, in particular zero, as compared to the second dialysis fluid rate.

The apparatus according to the present invention for extra-corporeal blood treatment has means for withdrawing ultrafiltrate from the chamber of the dialyser or filter through the semi-permeable membrane of the dialyser or filter at a preset ultrafiltrate flow rate $U_f$ in a first mode of operation and means for feeding dialysis fluid through one of the chambers of the dialyser or filter at a preset dialysis fluid flow rate $Q_d$ in a second mode of operation, the flow of fluid into the chamber of the dialyser or filter being interrupted in the first mode of operation, which means that dialysis fluid does not flow through the chamber or only a small dialysis fluid rate is set. The blood treatment apparatus is thus able to be operated essentially only as a haemofiltration apparatus in the first mode of operation and as a haemodiafiltration apparatus in the second mode of operation.

It is immaterial to the present invention what form the means for feeding dialysis fluid and withdrawing ultrafiltrate take. These means are therefore understood to be any means which are suitable for these purposes. It is also immaterial to the present invention how dialysis fluid and substitute are obtained and fed.

The control and computing unit of the extra-corporeal blood treatment apparatus has means for presetting an initial mode of treatment which takes place only during the opening phase of the blood treatment. The means for presetting the initial mode of treatment are so designed that substitute is fed to the extra-corporeal blood circuit at a preset substituate flow rate $Q_s$ over a preset interval of time, but dialysis fluid is not fed or at least only fed at a small dialysis fluid flow rate through the dialysis-fluid chamber of the dialyser or filter and instead essentially only ultrafiltrate is withdrawn through the membrane of the dialyser. On expiry of the first interval of time, the means for feeding dialysis fluid and withdrawing ultrafiltrate switch over to a mode of treatment which follows on from the initial mode of treatment and in which the means for feeding dialysis fluid and withdrawing ultrafiltrate are operated in a different mode of operation, so that dialysis fluid is only now fed, or from now on dialysis fluid is fed at a greater dialysis fluid rate, through the second chamber of the dialyser or filter. In the extra-corporeal blood treatment, the means for presetting the initial mode of treatment ensure that the rate of removal of electrolytes, and in particular of potassium, or of urea, is limited to safe levels, and there is thus little risk of the complications mentioned, and particularly the disequilibrium syndrome, occurring during the blood treatment.

In a preferred exemplary embodiment, the means for presetting the initial mode of treatment are so designed that the means for feeding in substituate and withdrawing substituate over the preset interval of time in which the blood treatment apparatus is operated essentially only as a haemofiltration apparatus are operated in such way that the substituate flow rate $Q_s$ is increased over the interval of time. The substituate flow rate is preferably increased continuously over the interval of time at a constant rate of increase, preferably from a substituate flow rate $Q_s=0$. It is however also possible for the substituate flow rate to be increased continuously at an increasing rate of increase. The substituate flow rate $Q_s$ may for example be increased exponentially. Over the interval of time, the substituate flow rate is increased from a starting value which is preferably zero, but may equally well be greater than zero, to a preset target value.

In an exemplary embodiment which is a particular preference, the means for presetting the initial mode of treatment are so designed that, on expiry of the preset interval of time in which the blood treatment apparatus is operated essentially only as a haemofiltration apparatus, the means for feeding dialysis fluid and withdrawing ultrafiltrate are, over a second preset interval of time which follows on directly from the first interval of time, operated in such a way that the dialysis fluid flow rate $Q_d$ is increased to a preset value. The dialysis fluid flow rate $Q_d$ can be increased over the preset interval of time continuously at a constant rate of increase or continuously at an increasing rate of increase, such as exponentially for example. The increase in the dialysis fluid flow rate takes place to a preset target value at which the blood treatment is to be continued. With the alternative embodiment, the dialysis fluid flow rate can also be increased continuously in the second time interval with a uniform rate of increase or continuously with an increasing rate of increase. The increase can take place, for example, starting from a dialysis fluid flow rate which is greater than the dialysis fluid flow rate set in the first time interval.

What is achieved by the adjustment of the dialysis fluid flow rate is a continuous transition from pure haemofiltration to haemodiafiltration, which has a beneficial effect on the patient's well-being.

A further exemplary embodiment of the present invention which is a particular preference makes provision for an input unit on which the patient himself can, in particular, make inputs by which the length of the first interval of time is preset. The input unit may for example be so designed that the patient is able to select one interval of time from two or more preset intervals of time of different lengths. It is however also possible that the patient may be able to shorten or lengthen, i.e., set, the length of the interval of time continuously. Any input means are a possibility for this purpose. The input unit gives the patient an opportunity to preset the length of the first interval of time as a function of how he is feeling at the time.

By presetting a long interval of time of for example 60 minutes, the patient may for example preset a "soft transition," thus making the risk of the disequilibrium syndrome occurring particularly low. However, by setting a shorter interval of time, such as 30 minutes for example, the patient may equally well preset a "harder transition," meaning that, although the extra-corporeal blood treatment is more effective during the opening phase than when the "softer transition" is set and the risk of the disequilibrium syndrome occurring is therefore higher, this risk is nevertheless still low.

On expiry of the first and second preset intervals of time, the haemodiafiltration treatment may be continued in a known manner, the dialysis fluid flow rate and/or ultrafiltrate flow rate and/or substituate flow rate being set in a known way with due allowance made for different considerations. What is important to the present invention is that, regardless of what flow rates are set for the fluids for the blood treatment, an initial mode of treatment, in which the risk of the disequilibrium syndrome occurring is very much reduced, is preset automatically in the opening phase of the blood treatment.

Exemplary embodiments of the present invention will be described in detail below with reference to the accompanying drawings.

DETAILED DESCRIPTION

Figure 1:
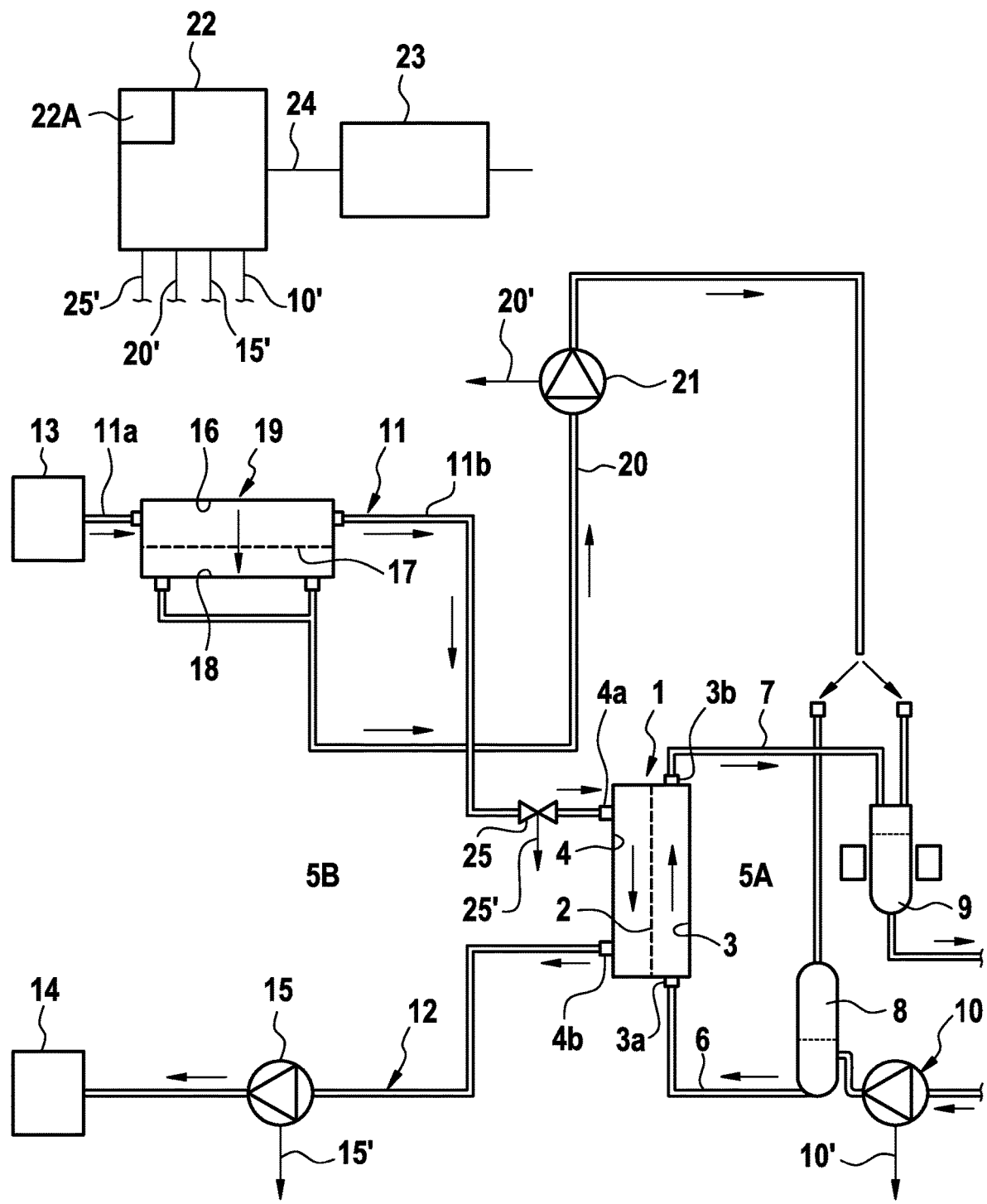
FIG. 1 is a highly simplified schematic view of the main components of the apparatus according to the present invention for extra-corporeal blood treatment.

FIG. 1 is a simplified schematic view of the main components of a haemodiafiltration apparatus.

The haemodiafiltration apparatus has a dialyser or filter 1 which is divided by a semi-permeable membrane 2 into a first chamber 3 through which blood flows and a second chamber 4 through which dialysis fluid flows. If the haemodiafiltration apparatus is operated as a haemofiltration apparatus, the dialyser acts as a filter.

The extra-corporeal blood circuit 5A comprises an arterial blood line 6 which runs from the patient to the inlet 3a of the blood chamber 3, and a venous blood line 7 which leads from the outlet 3b of the blood chamber 3 and runs to the patient. To minimise any air bubbles, an arterial drip chamber 8 is provided in the arterial blood line 6 and a venous drip chamber 9 is provided in the venous blood line 7. The patient's blood is fed through the blood chamber 3 of the dialyser 1 by an arterial blood pump 10 which is arranged in the arterial blood line 6.

The fluid system 5B comprises a dialysis-fluid infeed line 11 which runs to the inlet 4a of the dialysis-fluid chamber 4 of the dialyser 1, and a dialysis-fluid outfeed line 12 which leads from the outlet 4b of the dialysis-fluid chamber 4 of the dialyser 1. Fresh dialysis fluid flows from a dialysis fluid source 13 via the dialysis-fluid infeed line 11 into the dialysis-fluid chamber 4, while used dialysis fluid is taken away from the dialysis-fluid chamber 4, via the dialysis-fluid outfeed line 12, to a discharge 14. The dialysis fluid is fed by a dialysis-fluid pump 15 arranged in the dialysis-fluid outfeed line 12. Arranged in the dialysis-fluid infeed line 11 is a shut-off member 25 by which the infeed of dialysis fluid to the second chamber of the dialyser, and hence the flow of fluid through the second chamber of the dialyser, can be interrupted.

For greater clarity, the balancing arrangement for balancing fresh dialysis fluid against used dialysis fluid which is generally provided in haemodiafiltration apparatus has not been shown. Nor have additional facilities been shown, which may for example comprise means for cleaning and flushing the system, bypass lines, and further shut-off members.

The dialysis-fluid infeed line 11 comprises a first portion 11a, which runs to the inlet of a first chamber 16 of a sterile filter 19 which is divided into the first chamber 16 and a second chamber 18 by a membrane 17, and a second portion 11b which leads from the outlet of the first chamber 16 of the filter 19 and runs to the inlet 4a of the dialysis-fluid chamber 4.

During the blood treatment, dialysis fluid can be fed from the dialysis fluid system 5B to the extra-corporeal blood circuit 5A as substituate via a substituate line 20 which leads from the second chamber 18 of the filter 19. The substituate line 20 can be connected to the drip chamber 8 upstream of the blood chamber 3 or to the drip chamber 9 downstream of the blood chamber 3, thus enabling substituate to be fed either to the arterial blood line 6 upstream of the dialysis-fluid chamber 3 (pre-dilution) or to the venous blood line 7 downstream of the blood chamber 3 (post-dilution). The substituate is fed by a substituate pump 21 which is arranged in the substituate line 20.

The haemodiafiltration apparatus has a central computing and control unit 22 which performs all the controlling operations on the individual components of the blood treatment apparatus which are required for the extra-corporeal blood treatment. The central computing and control unit 22 may comprise one or more component parts. It may comprise one or more microprocessors which are programmed in such a way that the individual components of the blood treatment apparatus are operated.

The central control and computing unit 22 is connected by a control line 10' to the blood pump 10, by a control line 15' to the dialysis-fluid pump 15, by a control line 20' to the substituate pump 21 and by a control line 25' to the shut-off member 25, thus enabling the individual pumps 10, 15, 21 to be switched on and off and the shut-off member 25 to be opened and closed and different feed rates to be set for the individual pumps.

As well as this, the haemodiafiltration apparatus also has an input unit 23 (only schematically indicated) which is connected by a data line 24 to the control and computing unit 22. The input unit 23 may for example be a touch screen or a keyboard. The input unit 23 may also be a unit having one or more switches or controls which the medical staff or the patient himself can use to make settings for the blood treatment.

The central computing and control unit 22 has means 22A for presetting an initial mode of treatment during the opening phase of the treatment. These means may be part of the control system for the apparatus. The means may for example be a computer program (software) which runs on the computing and control unit 22. The means may however also take the form of hardware.

At the beginning of the blood treatment, the computing and control unit 22 starts a first timer which presets a first interval of time $\Delta T_1$ which is for example between 30 and 60 minutes long. Over the first interval of time $\Delta T_1$, with the shut-off member 25 in the dialysis-fluid infeed line 11 closed, the substituate pump 21 is operated in such a way that the pump feeds substituate at a preset substituate flow rate Qs, and the dialysis-fluid pump 15 withdraws ultrafiltrate from the dialysis-fluid chamber 4 through the semi-permeable membrane 2 of the dialyser 1 or filter. The thing that is important is that dialysis fluid is no longer fed through the dialysis-fluid chamber of the dialyser. Consequently, the haemodiafiltration apparatus is operated purely as a haemofiltration apparatus during the first interval of time.

During the first interval of time $\Delta T_1$, the substituate flow rate $Q_s$ is increased, preferably from $Q_s=0$ to a target value $Q_s!$. In a first exemplary embodiment, the substituate flow rate $Q_s$ is increased from zero to the target value continuously at a constant rate of increase. In an alternative exemplary embodiment, the substituate flow rate is increased continuously at an increasing rate of increase, and in particular exponentially, during the first interval of time $\Delta T_1$.

Because only a convective and not a diffusive metabolic exchange takes place during the first interval of time, the exchange rate of electrolytes such as potassium or of urea is reduced. This reduces the risk of disequilibrium syndrome occurring.

On expiry of the first interval of time, the means for presetting the initial mode of treatment switch over from pure haemofiltration to haemodiafiltration in which dialysis fluid flows through the second chamber of the dialyser and ultrafiltrate is withdrawn from the dialysis fluid chamber and substituate can be supplied to the extracorporeal blood circuit. However, the switchover does not take place abruptly but continuously, in that a second interval of time $\Delta T_2$, which is preset by a second timer, begins to run on expiry of the first interval of time.

On expiry of the first interval of time, the shut-off member 25 is opened, and the blood treatment apparatus can thus be operated again as a haemodiafiltration apparatus. Over the second interval of time $\Delta T_2$, the dialysis fluid flow rate $Q_d$ is increased from a value $Q_d=0$ to a target value $Q_d!$ at which the blood treatment is to be carried out on expiry of the second interval of time. The target value may be constant during the blood treatment, or again it may be altered. The increase in the dialysis-fluid flow rate may once again take place at a constant rate of increase in the form of a ramp or at increasing rate of increase, and in particular exponentially.

On expiry of the second interval of time $\Delta T_2$, the setting takes place of the fluid flow rates for the blood treatment, as specified by the physician. Action on the system controlling the fluid flow rates is only taken during the opening phase $\Delta T = \Delta T_1 + \Delta T_2$ of the blood treatment.

A preferred exemplary embodiment of the present invention makes provision for the patient himself to be able to make presettings for the first interval of time $\Delta T_1$ on the input unit 23. In this way, the patient may for example shorten or lengthen the first interval of time as a function of how he feels at the time.

Figure 2:
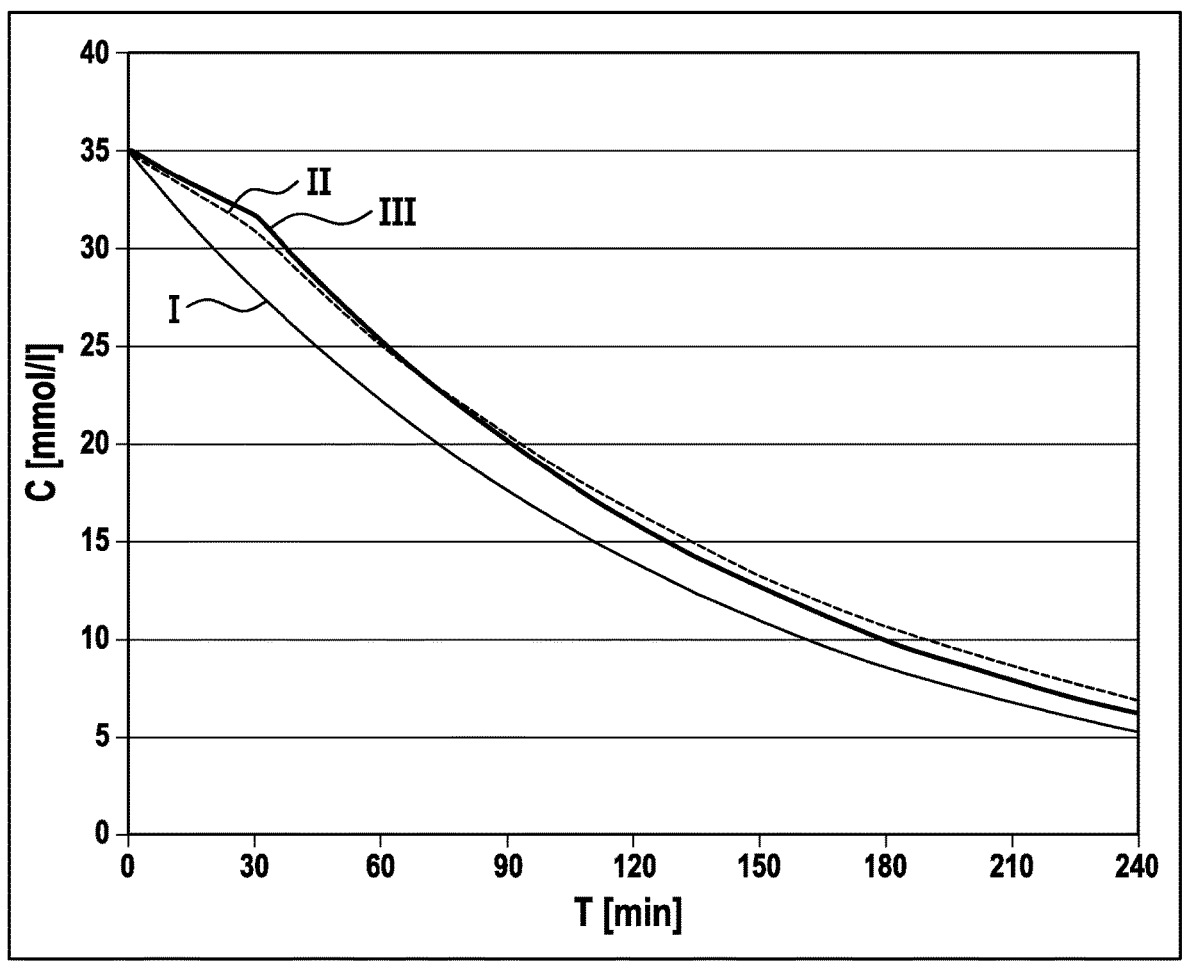
FIG. 2 shows urea concentration as a function of treatment time.

FIG. 2 shows urea concentration C [mmol/l] as a function of the treatment time T [min] for different types of treatment. A haemodiafiltration treatment with post-dilution, carried out with a conventional blood treatment apparatus and making no provision for an initial mode of treatment, is shown as curve I in FIG. 2, a haemodiafiltration treatment with pre-dilution which is preceded by an initial mode of treatment in which haemofiltration with pre-dilution is given is shown as curve II, and a haemodiafiltration treatment with post-dilution which is preceded by an initial mode of treatment in which haemofiltration with post-dilution is given is shown as curve III.

It can be seen that in the opening phase of the treatment, and in particular over a period from 0 to 60 minutes, there is a particularly sharp decrease in the urea concentration. Towards the end of the treatment, the urea concentration decreases less sharply. This can be seen from the fact that the curve is steeper in the opening phase of the treatment than in the final phase. What is achieved with the apparatus and method according to the present invention is that it is precisely in the opening phase of the treatment that the decrease in urea concentration is reduced, by operating the blood treatment apparatus only as a haemofiltration apparatus, preferably at an increasing substitute flow rate.

In an alternative exemplary embodiment of the present invention, a dialysis fluid flow rate is not set at zero in the initial treatment mode, i.e., the fluid flow through the dialysis fluid chamber 4 of the dialyser is not interrupted. As a result, the shut-off member 25 need not be present in this exemplary embodiment. In the first predetermined time interval, a dialysis fluid flow rate is set that is smaller than the dialysis fluid flow rate in the subsequent second time interval. In the first time interval, dialysis fluid flow rates can be set, for example, that are less than 100 ml/min, preferably 50 ml/min. In the second time interval, a dialysis fluid flow rate of, e.g., 500 ml/min can be set with an alternative exemplary embodiment. Dialysis fluid flow rates greater than 270 ml/min are particularly preferred. The alternative exemplary embodiment works on the assumption that the dialysis fluid flow through the second chamber in the initial treatment mode need not necessarily be completely interrupted.

What is claimed is:

1. An apparatus for extra-corporeal blood treatment, the apparatus comprising an extra-corporeal blood circuit, a fluid system, a substitute pump, and a dialyser or filter, the dialyser or filter being divided into a first chamber and a second chamber by a semi-permeable membrane, the extra-corporeal blood circuit including the first chamber and comprising a blood pump configured for feeding blood through the first chamber, the fluid system including the second chamber, the apparatus further comprising:

a dialysis-fluid pump configured for feeding dialysis fluid through the second chamber of the dialyser or filter, and a valve configured for interrupting fluid flow into the second chamber of the dialyser or filter, wherein the dialysis-fluid pump and the valve are configured to operate according to a first operating mode and a second operating mode and configured to switch over from the first operating mode to the second operating mode continuously, but not abruptly, wherein, the first operating mode is carried out over a first preset interval of time, in the first operating mode ultrafiltrate is withdrawn from the second chamber of the dialyser or filter and fluid flow into the second chamber of the dialyser or filter is interrupted, substituate is fed with the substituate pump into the extra-corporeal blood circuit over the first preset interval of time and at a preset substituate flow rate or at a preset progression of a substituate flow rate, and, during the switch over to the second operating mode, dialysis fluid is fed through the second chamber of the dialyser or filter over a second preset interval of time while the dialysis-fluid pump is controlled to increase a flow rate of dialysis fluid pumped through the second chamber, over the second preset interval of time, from an initial dialysis-fluid flow rate of zero to a target dialysis fluid flow rate, wherein the substituate pump is configured for feeding substituate into the extra-corporeal blood circuit upstream or downstream of the dialyser or filter; and a control and computing unit comprising a first timer setting the first preset interval of time and a second timer setting the second preset interval of time, the control and computing unit being configured to preset the first operating mode of treatment during the first preset interval of time, and the control and computing unit is configured such that:

within the first preset interval of time, the substituate pump is operated such that substituate is fed to the extra-corporeal blood circuit at the preset substituate flow rate or the preset progression of the substituate flow rate, the dialysis-fluid pump and the valve are operated such that, during the first operating mode, the valve is closed and dialysis fluid is not fed through the second chamber of the dialyser or filter, and ultrafiltrate is withdrawn from the second chamber through the semi-permeable membrane of the dialyser or filter while fluid flow into the second chamber of the dialyser or filter is interrupted; and on expiry of the first preset interval of time, the switch over to the second mode of treatment is initiated continuously, but not abruptly, in which the dialysis-fluid pump and the valve are operated over the second preset interval of time until the second operating mode is commenced, such that dialysis fluid is fed through the second chamber of the dialyser or filter at the target dialysis fluid flow rate, wherein the first operating mode and the switch over to the second operating mode are configured to prevent disequilibrium syndrome.

2. The apparatus according to claim 1, wherein the control and computing unit is configured such that the substituate pump is operated such that the substituate flow rate is increased within the first preset interval of time.

3. The apparatus according to claim 2, wherein the substituate pump is operated such that the substituate flow rate is increased continuously over the first preset interval of time at a constant rate of increase.

4. The apparatus according to claim 2, wherein the substitute pump is operated such that the substitute flow rate is increased continuously over the first preset interval of time at an increasing rate of increase.

5. The apparatus according to claim 1, wherein the control and computing unit is configured such that on expiry of the first preset interval of time, the dialysis-fluid pump and the valve are operated such that, over the second preset interval of time, a dialysis fluid flow rate is increased to a preset value.

6. The apparatus according to claim 5, wherein the dialysis-fluid pump and the valve are operated such that the dialysis fluid flow rate is increased continuously over the second preset interval of time at a constant rate of increase.

7. The apparatus according to claim 5, wherein the dialysis-fluid pump and the valve are operated such that the dialysis fluid flow rate is increased continuously over the second preset interval of time at an increasing rate of increase.

8. The apparatus according to claim 1, further comprising:
an input unit configured to at least one of input a length of the first preset interval of time or change the length of the first preset interval of time.

9. The apparatus according to claim 1, wherein the extra-corporeal blood circuit includes a blood infeed line which runs to the first chamber of the dialyser or filter, and a blood outfeed line which leads from the first chamber of the dialyser or filter, and the fluid system includes a dialysis-fluid infeed line which runs to the second chamber of the dialyser or filter, and a dialysis-fluid outfeed line which leads from the second chamber of the dialyser or filter, the valve being arranged in the dialysis-fluid infeed line and the dialysis-fluid pump being arranged in the dialysis-fluid outfeed line.

10. The apparatus according to claim 9, wherein the fluid system includes a substitute line running to the blood infeed line or blood outfeed line, the substitute pump being arranged in the substitute line.

11. A method of carrying out an extra-corporeal blood treatment using an extra-corporeal blood treatment apparatus, the apparatus comprising an extra-corporeal blood circuit, a fluid system, a substitute pump, and a dialyser or filter, the dialyser or filter being divided into a first chamber and a second chamber by a semi-permeable membrane, the fluid system including the second chamber of the dialyser or filter and comprising a dialysis-fluid pump, the extra-corporeal blood circuit including the first chamber of the dialyser or filter and comprising a blood pump configured for feeding blood through the first chamber of the dialyser or filter in the extra-corporeal blood circuit, the method comprising:
setting a first preset interval of time and a second preset interval of time;
operating the extra-corporeal blood treatment apparatus in a first operating mode over the first preset interval of time, as a haemofiltration apparatus, the first operating mode comprising (i) withdrawing, with the dialysis-fluid pump, ultrafiltrate from the second chamber of the dialyser or filter while a fluid flow into the second chamber of the dialyser or filter is interrupted by a valve, and (ii) feeding substitute, with the substitute pump, into the extra-corporeal blood circuit upstream or downstream of the dialyser or filter over the first preset interval of time and at a preset substitute flow rate or at a preset progression of a substitute flow rate;
on expiry of the first preset interval of time, switching over continuously, but not abruptly, operation of the extra-corporeal blood treatment apparatus to a second operating mode as a haemodiafiltration apparatus, the switching over comprising (a) opening the valve, (b) pumping, with the dialysis-fluid pump, dialysis fluid through the second chamber of the dialyser or filter, and (c) operating the dialysis-fluid pump so as to increase a flow rate of dialysis fluid pumped through the second chamber, over the second preset interval of time, from an initial dialysis-fluid flow rate of zero to a target dialysis fluid flow rate; and
on expiry of the second preset interval of time, operating the extra-corporeal blood treatment apparatus in the second operating mode wherein the dialysis-fluid pump pumps dialysis fluid at the target dialysis-fluid flow rate,
wherein the first operating mode and the switch over to the second operating mode are configured to prevent disequilibrium syndrome.

12. The method according to claim 11, wherein the substitute flow rate is increased over the first preset interval of time.

13. The method according to claim 12, wherein the substitute flow rate is increased continuously over the first preset interval of time at a constant rate of increase.

14. The method according to claim 12, wherein the substitute flow rate is increased continuously over the first preset interval of time at an increasing rate of increase.

15. The method according to claim 11, wherein, on expiry of the first preset interval of time, a dialysis fluid flow rate is increased constantly to the target dialysis fluid flow rate over the second preset interval of time.

16. The method according to claim 15, wherein the dialysis fluid flow rate is increased continuously over the second preset interval of time, at a constant rate of increase.

17. The method according to claim 15, wherein the dialysis fluid flow rate is increased continuously over the second preset interval of time, at an increasing rate of increase.

18. An apparatus for extra-corporeal blood treatment, the apparatus comprising an extra-corporeal blood circuit, a fluid system, a substitute pump, and a dialyser or filter, the dialyser or filter being divided into a first chamber and a second chamber by a semi-permeable membrane, the extra-corporeal blood circuit including the first chamber and comprising a blood pump configured for feeding blood through the first chamber, the fluid system including the second chamber, the apparatus further comprising:
a dialysis-fluid pump configured for feeding dialysis fluid through the second chamber of the dialyser or filter, and a valve configured for interrupting fluid flow into the second chamber of the dialyser or filter, wherein the dialysis-fluid pump and the valve are configured to operate according to a first operating mode and a second operating mode and configured to switch over from the first operating mode to the second operating mode continuously, but not abruptly,
wherein, in the first operating mode, ultrafiltrate is withdrawn from the second chamber of the dialyser or filter and dialysis fluid is fed through the second chamber of the dialyser or filter at a first dialysis fluid flow rate over a first preset interval of time while substitute is fed, with the substitute pump, into the extra-corporeal blood circuit over the first preset interval of time and at a preset substitute flow rate or at a preset progression of a substitute flow rate, and, during the switch over to the second operating mode, dialysis fluid flow is increased through the second chamber of the dialyser or filter over a second preset interval of time, to a target, second dialysis fluid flow rate, wherein the first dialysis fluid flow rate is smaller than the second dialysis fluid flow rate, wherein the first dialysis fluid flow rate is smaller than the second dialysis fluid flow rate, wherein the substituate pump is configured for feeding substituate into the extra-corporeal blood circuit upstream or downstream of the dialyser or filter; and a control and computing unit comprising a first timer setting a first interval of time and a second timer setting a second interval of time, the control and computing unit being configured to preset an initial mode of treatment, and the control and computing unit being configured such that:

within the first preset interval of time, the substituate pump is operated such that substituate is fed to the extra-corporeal blood circuit at the preset substituate flow rate or the preset progression of the substituate flow rate, the dialysis-fluid pump and the valve are operated such that the valve is opened and ultrafiltrate is withdrawn from the second chamber through the semi-permeable membrane of the dialyser or filter and dialysis fluid is fed through the second chamber at the first dialysis fluid flow rate; and on expiry of the first preset interval of time, the switch over to the a second mode of treatment is initiated continuously, but not abruptly, such that the dialysis-fluid pump and the valve are operated over the second preset interval of time until the second operating mode is initiated and dialysis fluid is fed through the second chamber of the dialyser or filter at the second dialysis fluid flow rate, wherein the first operating mode and the switch over to the second operating mode are configured to prevent disequilibrium syndrome.

19. A method of carrying out an extra-corporeal blood treatment using an extra-corporeal blood treatment apparatus, the apparatus comprising an extra-corporeal blood circuit, a fluid system, a substituate pump, and a dialyser or filter, the dialyser or filter being divided into a first chamber and a second chamber by a semi-permeable membrane, the fluid system including the second chamber of the dialyser or filter and comprising a dialysis-fluid pump, the extra-corporeal blood circuit including the first chamber of the dialyser or filter and comprising a blood pump configured for feeding blood through the first chamber of the dialyser or filter in the extra-corporeal blood circuit, the method comprising:

setting a first preset interval of time and a second preset interval of time;

operating the extra-corporeal blood treatment apparatus in a first operating mode over the first preset interval of time, as a haemofiltration apparatus, the first operating mode comprising (i) withdrawing, with the dialysis-fluid pump, ultrafiltrate from the second chamber of the dialyser or filter while using a valve to control a fluid flow into the second chamber of the dialyser or filter at a dialysis fluid flow rate of greater than zero to less than 100 ml/min, and (ii) feeding substituate, with the substituate pump, into the extra-corporeal blood circuit upstream or downstream of the dialyser or filter over the first preset interval of time and at a preset substituate flow rate or a preset progression of a substituate flow rate;

on expiry of the first preset interval of time, switching over continuously, but not abruptly, operation of the extra-corporeal blood treatment apparatus to a second operating mode as a haemodiafiltration apparatus, the switching over comprising (a) increasing fluid flow through the valve, (b) pumping, with the dialysis-fluid pump, dialysis fluid through the second chamber of the dialyser or filter, and (c) operating the dialysis-fluid pump so as to increase the flow rate of dialysis fluid pumped through the second chamber, over the second preset interval of time, to a target dialysis fluid flow rate; and on expiry of the second preset interval of time, operating the extra-corporeal blood treatment apparatus in the second operating mode wherein the dialysis-fluid pump pumps dialysis fluid at the target dialysis-fluid flow rate, wherein the first operating mode and the switch over to the second operating mode are configured to prevent disequilibrium syndrome.

20. The method according to claim 19, wherein the target dialysis fluid flow rate is greater than 270 ml/min.

21. The method according to claim 19, wherein the substituate flow rate is increased over the first preset interval of time.

22. The method according to claim 21, wherein the substituate flow rate is increased continuously over the first preset interval of time at a constant rate of increase.

23. The method according to claim 21, wherein the substituate flow rate is increased continuously over the first preset interval of time at an increasing rate of increase.

24. The method according to claim 19, wherein, on expiry of the first preset interval of time, a dialysis fluid flow rate is increased constantly to the target dialysis fluid flow rate over the second preset interval of time.

25. The method according to claim 24, wherein the dialysis fluid flow rate is increased continuously over the second preset interval of time, at a constant rate of increase.

26. The method according to claim 24, wherein the dialysis fluid flow rate is increased continuously over the second preset interval of time, at an increasing rate of increase.

27. The apparatus of claim 18, wherein the first dialysis fluid flow rate is less than 100 ml/min.

* * * * *